US009872871B2

(12) United States Patent
Jeppesen et al.

(10) Patent No.: US 9,872,871 B2
(45) Date of Patent: Jan. 23, 2018

(54) COMPOSITIONS FOR USE IN RESTORING MUSCLE GLYCOGEN AND/OR MUSCLE MASS

(71) Applicant: Aarhus Universitet, Aarhus C (DK)

(72) Inventors: Per Bendix Jeppesen, Egå (DK); Søren Lavrsen, Silkeborg (DK)

(73) Assignee: Aarhus Universitet, Aarhus C (DK)

( * ) Notice: Subject to any disclaimer, the term of this patent is extended or adjusted under 35 U.S.C. 154(b) by 0 days.

(21) Appl. No.: 14/786,238

(22) PCT Filed: Apr. 22, 2014

(86) PCT No.: PCT/DK2014/050105
§ 371 (c)(1),
(2) Date: Oct. 22, 2015

(87) PCT Pub. No.: WO2014/173418
PCT Pub. Date: Oct. 30, 2014

(65) Prior Publication Data
US 2016/0074424 A1  Mar. 17, 2016

(30) Foreign Application Priority Data
Apr. 23, 2013  (DK) .................... 2013 70226

(51) Int. Cl.
| A61K 31/704 | (2006.01) |
| A61K 31/716 | (2006.01) |
| A23L 33/105 | (2016.01) |
| A61K 9/00 | (2006.01) |
| A23L 2/52 | (2006.01) |
| A61K 47/36 | (2006.01) |
| A61K 47/42 | (2017.01) |
| A23L 33/11 | (2016.01) |

(52) U.S. Cl.
CPC .............. *A61K 31/704* (2013.01); *A23L 2/52* (2013.01); *A23L 33/105* (2016.08); *A23L 33/11* (2016.08); *A61K 9/0056* (2013.01); *A61K 9/0095* (2013.01); *A61K 31/716* (2013.01); *A61K 47/36* (2013.01); *A61K 47/42* (2013.01); *A23V 2002/00* (2013.01)

(58) Field of Classification Search
CPC .. A61K 31/704; A61K 9/0095; A61K 9/0056; A23L 33/105
See application file for complete search history.

(56) References Cited

U.S. PATENT DOCUMENTS

| 2003/0170346 A1 | 9/2003 | McCabe | |
| 2004/0022914 A1* | 2/2004 | Allen | A23L 33/105 426/548 |
| 2006/0002983 A1 | 1/2006 | Matsumoto et al. | |
| 2007/0160698 A1* | 7/2007 | Waga | A61K 31/121 424/765 |
| 2007/0172510 A1 | 7/2007 | Melton | |
| 2009/0162486 A1 | 6/2009 | Kowalczyk et al. | |
| 2012/0116069 A1 | 5/2012 | Iwasaki et al. | |

FOREIGN PATENT DOCUMENTS

| WO | WO 01/56959 A1 | 8/2001 |
| WO | WO 2006/116814 A1 | 11/2006 |
| WO | WO 2012/032544 A2 | 3/2012 |

OTHER PUBLICATIONS

Jeppesen et al; "Stevioside induces antihyperglycaemic, insulinotropic and glucagonostatic effects in vivo; studies in the diabetic Goto-Kakizaki (GK) rats"; Phytomedicine, Gustav Fisher Verlag, Stuttgart, DE; vol. 9, No. 1, Jan. 1, 2002, pp. 9-14.
Lailerd, et al; "Effects of Stevioside on Glucose TransportActivity in Insulin-Sensitive and Insulin-Resistant Rat Skeletal Muscle"; Metabolism: Clinical and Experimental Jan. 2004; vol. 53, No. 1, Jan. 2004, pp. 101-107.
Beelen, et al; "Nutritional Strategies to Promote Postexercise Recovery"; International Journal of Sport Nutrition and Exercise Metabolism; vol. 20, 2010; pp. 515-532.
Blom, et al; "Effect of different post-exercise sugar diets on the rate of muscle glycogen synthesis"; Medicine and Science in Sports and Exercise; vol. 19; No. 5, 1987; pp. 491-496.
Burke, et al; "Carbohydrates and fat for training and recovery"; Journal of Sports Sciences, vol. 22, 2004, pp. 15-30.
Carmeli, et al; "The biochemistry of aging muscle"; Experimental Gerontology vol. 37, 2002; pp. 477-489.
Carrithers, et al; "Effects of postexercise carbohydrate-protein feedings on muscle glycogen restoration"; J. Appl. Physiol., vol. 88, 2000, pp. 1976-1982.
Chiang, et al; "Mechanism of Hypoxia-induced GCM1 Degradation", The Journal of Biological Chemistry; vol. 284; No. 26; Jun. 26, 2009, pp. 17411-17419.
Costill, et al; "Carbohydrate Nutrition and Fatigue"; Sports Medicine, vol. 13, No. 2, 1992, pp. 86-92.
Coyle, et al; "Muscle glycogen utilization during prolonged strenuous exercise when fed carbohydrate"; The American Physiological Society; 0161-7567/86; 1986, pp. 165-172.
Fujita, et al; "Aerobic Exercise Overcomes the Age-Related Insulin Resistance of Muscle Protein Metabolism by Improving Endothelial Function and Akt/Mammalian Target of Rapamycin Signaling"; Diabetes, vol. 56, Jun. 2007, pp. 1615-1622.
Gregersen, et al; "Antihyperglycemic Effects of Stevioside in Type 2 Diabetic Subjects"; Metabolism, vol. 53, No. 1, Jan. 2004; pp. 73-76.
Hermansen, et al; "Muscle Glycogen during Prolonged Severe Exercise"; Acta Plysiol. Scand.; vol. 71:2-3, pp. 129-139.
Ivy, et al; "Muscle glycogen storage after different amounts of carbohydrate ingestion"; The American Physiological Society, 0161-7567/88, 1988, pp. 2018-2023.

(Continued)

*Primary Examiner* — Jonathan S Lau
(74) *Attorney, Agent, or Firm* — Posternak Blankstein & Lund LLP

(57) ABSTRACT

The present invention relates to compositions comprising a steviol glycoside for use in restoring muscle glycogen by increasing the rate of glycogen re-synthesis in muscles that are depleted in glycogen due to exhaustive exercise and/or for use in treatment of muscle mass by increasing the rate of protein synthesis in muscles that are depleted in protein mass.

15 Claims, 4 Drawing Sheets

(56) References Cited

OTHER PUBLICATIONS

Jeffrey and Huang; "The tetrasaccharide nystose trihydrate: Crystal structure analysis and hydrogen bonding"; Carbohydrate Research, vol. 247, 1993, pp. 37-50.
Jeffreyand Pain; "Stimulation by insulin of protein synthesis in cultured chick embryo fibroblasts"; Biochimie, vol. 75, 1993, pp. 791-796.
Jeppesen, et al; "Can Stevioside in Combination with a Soy-Based Dietary Supplement Be a New Useful Treatment in Type 2 Diabetes? An In Vivo Study in the Diabetic Goto-Kakizaki Rat"; Rev. Diabetic. Stud., vol. 3, No. 4, 2006, pp. 189-199.
Rottenberg, et al; "Glycogen-Mediated Activation of Pig-Brain Glycogen Synthetase I and D"; Biochemical and Biophysical Research Communications, vol. 48, No. 5, 1972, pp. 1192-1198.
Reed, et al; "Muscle glycogen storage postexercise: effect of mode of carbohydrate administration"; The American Physiological Society; 0161-7567/89, 1989, pp. 720-726.
Suanarunsawat, et al; "The effect of stevioside on glucose metabolism in rat"; Can. J. Physiol. Pharmacol., vol. 75, 1997, pp. 976-982.
Toskulkao, et al; "Inhibitory effect of steviol, a metabolite of stevioside, on glucose absorption in everted hamster intestine in vitro"; Toxicology Letters, vol. 80, 1995, pp. 153-159.
Vandenbogaerde, et al; "Effects of Acute Carbohydrate Supplementation on Endurance Performance: A Meta-Analysis"; Sports Med. vol. 41, No. 9, 2011, pp. 773-792.

\* cited by examiner

COMPOSITIONS FOR USE IN RESTORING MUSCLE GLYCOGEN AND/OR MUSCLE MASS

FIELD OF INVENTION

The present invention relates to compositions comprising a steviol glycoside for use in restoring muscle glycogen by increasing the rate of glycogen re-synthesis in muscles that are depleted in glycogen due to exhaustive exercise and/or for use in restoring muscle mass by increasing the rate of protein synthesis.

BACKGROUND OF INVENTION

Glucose is the primary source of fuel for all body cells. After a meal, some of the glucose not used immediately for fuel travels to the liver or skeletal muscles, where it is converted to glycogen through the process glycogenesis, and stored for energy. Any excess glucose is stored in adipose tissue as fat. The liver has a greater capacity for glycogen storage than the muscles. Liver cells can typically store up to 8% of their weight as glycogen, while muscle cells can typically store up to only 3%. The liver is responsible for maintaining adequate levels of glucose in the body. As the body's glucose level drops, the liver converts some of the glycogen back into glucose through the process glycogenolysis and releases it back into the bloodstream. Muscle cells, on the other hand, are unable to reconvert glycogen to glucose. Instead, they convert glycogen directly to fuel through the process glycolysis.

Glycolysis is the cellular anaerobic process, which breaks down muscle glycogen into pyruvic acid during high-intensity exercise. This process rapidly produces a small amount of adenosine triphosphate (ATP), the necessary fuel for body cells. However, if too much pyruvic acid accumulates in the muscle during glycolysis, it can substantially slow down or even stop the process of ATP formation. Therefore, after one or two minutes of high-intensity exercise, a subsequent process of energy formation begins. This process is referred to as oxidation.

Oxidation produces over 95% of the energy used by muscles during moderate and prolonged exercise. Oxidation immediately converts much of the pyruvic acid formed through glycolysis to ATP. However, during prolonged exercise, if an athlete is unable to breathe in oxygen quickly enough to oxidize pyruvic acid into ATP, some pyruvic acid is converted to lactic acid and diffused out of the cell. It then circulates throughout the body until it can be reconverted to pyruvic acid once oxygen again becomes available. If excess accumulation of lactic acid occurs, extreme fatigue can set in, which can greatly impair the athlete's performance.

Glucose is needed by the central nervous system to keep the body functioning. Therefore, during periods of moderate exercise lasting longer than 20 minutes, the body works to conserve stored muscle and liver glycogen. It does so by reducing the percentage of fuel derived from glycogen to only 40% or 50%, with the remainder supplied by fat. During exercise periods lasting longer than 4 or 5 hours, as much as 60% to 85% of fuel produced by oxidation may be derived from fat.

Fats need carbohydrates in order to burn efficiently. The breakdown of carbohydrates generates oxaloacetic acid, which is needed for the breakdown of fats into fuel. If insufficient carbohydrate levels exist, the levels of oxaloacetic acid may also drop, making it difficult for the body to continue producing a high level of fuel from fat. Although the body can break down fats in the absence of carbohydrates, it does so at a much slower rate. When the glycogen stores in the muscles and liver are depleted, and the blood glucose level begins to fall, athletes begin to experience fatigue, lack of coordination, light-headedness and lack of concentration. This experience is commonly known as "hitting the wall" or "bonking".

During exhaustive exercise the aim is to increase sparing of muscle glycogen and thereby simultaneously extend endurance. There is a consensus that 8 to 10 g of carbohydrate per kg of body weight will maintain appropriate glycogen levels during heavy training.

Following exhaustive exercise, the body needs to replenish the depleted glycogen reserves. Furthermore, the muscle degradation during exercise requires protein to fully recover. It is therefore important to consume additional carbohydrate and protein after exercise. This should be done within the first two hours after exercise during the period known as "the muscle recovery window" or "the glycogen replacement window". This is because the enzyme glycogen synthase, which is responsible for restoring glycogen, is highly elevated immediately after exercise. A combination of carbohydrate and protein is recommended preferably together with water and electrolytes.

When the body has sustained a complete or a bear-total depletion of its glycogen stores, it will take approximately 24 hours for the body to both ingest sufficient food of the appropriate carbohydrate proportion as well as convert the ingested carbohydrates into glycogen.

The pattern of muscle glycogen synthesis following its depletion by exercise is biphasic. Initially, there is a rapid, insulin independent increase in the muscle glycogen stores. This is then followed by a slower insulin dependent rate of synthesis. Contributing to the rapid phase of glycogen synthesis is an increase in muscle cell membrane permeability to glucose, which serves to increase the intracellular concentration of glucose-6-phosphate (G6P) and activate glycogen synthase. Stimulation of glucose transport by muscle contraction as well as insulin is largely mediated by translocation of the glucose transporter isoform GLUT4 from intracellular sites to the plasma membrane. Thus, the increase in membrane permeability to glucose following exercise most likely reflects an increase in GLUT4 protein associated with the plasma membrane. This insulin-like effect on muscle glucose transport induced by muscle contraction, however, reverses rapidly after exercise is stopped. As this direct effect on transport is lost, it is replaced by a marked increase in the sensitivity of muscle glucose transport and glycogen synthesis to insulin. Thus, the second phase of glycogen synthesis appears to be related to an increased muscle insulin sensitivity. Although the cellular modifications responsible for the increase in insulin sensitivity are unknown, it apparently helps maintain an increased number of GLUT4 transporters associated with the plasma membrane once the contraction-stimulated effect on translocation has reversed. It is also possible that an increase in GLUT4 protein expression plays a role during the insulin dependent phase.

Muscle glycogen is an essential source of energy during endurance training and competition (Vandenbogaerde et al. 2011). Several studies have shown that depletion of muscle glycogen storages coincides with fatigue during prolonged physical activity (Hermansen et al. 1967, Coyle et al. 1986). Further it has been shown by Costill et al. that it is not possible to maintain a high aerobic power output after the muscle glycogen storages has been depleted (Costill et al. 1971). Thus, glycogen depletion impairs the performance in endurance sports disciplines such as long distance running, cycling, triathlon, cross-country skiing etc.

In line with this, it has been found that the ability to maintain optimal aerobic performance during long lasting endurance activities is directly dependent on the initial size of the muscles glycogen storage (Jeffrey et al. 1993). Furthermore, it has also been shown that a single exhaustive training session could be sufficient to deplete the glycogen storages to a degree which would have a negative impact on performance in a following session.

At a glycogen storage rate of 5-6 mmol/kg/ww/h it may take up to 24 hours, to replenish the glycogen storage after exhaustive exercise (Coyle et al. 1986), this is supported by results from numerous other studies (Blom et al. 1987; Ivy et al. 1988; Reed et al. 1989). In reality the demands of training and competition of many athletes offers considerably less time, for recovery, in between sessions. Since the potential for performance in subsequent training sessions in part depends on the recovery of muscle glycogen storage, some athletes may compromise performance by initiating training with inadequate glycogen storages in the working muscles. To ensure an optimal outcome of the individual training session and thereby the overall performance development of the athlete, an efficient resynthesis of the muscle glycogen storages, after an exhaustive training session, is of great importance. This is in particular important in athletes with a high training volume and/or several training sessions a day. Based on these challenges regarding recovery in elite sports, several methods to increase muscle glycogen storages have been investigated. Research in this area has focused mainly on: timing, frequency, type and amount of carbohydrate ingestion as well as co-ingestion of other macronutrients, mainly protein (Carrithers et al. 2000). To optimally restore muscle glycogen storages athletes are recommended to consume high amounts (>1.2 g/kg/h) of high glycemic carbohydrates immediately after exercise and the following 4-6 hours. In order to ensure optimal glycogen storage as well as to avoid gastrointestinal distress the ingestion of post exercise meals should be consumed at frequent intervals (evenly at every 15 to 30 minutes) during these initial 4 to 6 hours following exercise (Burke et al. 2004).

Insulin is known to play an important role in the promotion of glycogen synthesis in muscles (Beelen et al 2010). In effect, the rate of carbohydrate uptake across the plasma membrane of the muscle cells seems to be controlled by the rate of insulin secretion from the pancreas (Jeppesen et al. 2000). Therefore increasing pancreatic insulin secretion and/or increase insulin sensitivity in the muscle tissue might be important for optimizing cross-membrane glucose transport and hence glycogen resynthesis after exhaustive exercise training.

Both exercise and the secretion of insulin have been shown to increase the rate of glycogen resynthesis (Chiang et al. 2009). It appears that the effect of exercise and insulin work through pathways, independent of each other, and they might both might work to facilitate glycogen resynthesis in an additive manner (Chiang et al. 2009). It could be speculated that if insulin secretion and/or insulin sensitivity could be enhanced in the post exercise recovery period, then glycogen resynthesis may be increased, causing a faster recovery of muscle glycogen storages post exercise.

Research has been directed to how various diet impact muscle metabolism and performance. In particular research has been focused on the consumption of the combination of carbohydrate and proteins after strenuous exercise to enhance muscle glycogen restoration.

Carrithers et al. have investigated the effects of postexercise eucaloric carbohydrate-protein feedings on muscle glycogen restoration after an exhaustive cycle ergometer exercise bout. In the study 7 male collegiate cyclists performed 3 trials each separated by one week. The diet investigated were 1) 100% α-D-glucose, 2) 70% carbohydrate—20% protein—10% fat and 3) 86% carbohydrate—14% amino acids. The results of this study suggest that muscle glycogen restoration does not appear to be enhanced with the addition of proteins or amino acids to an eucaloric carbohydrate feeding after exhaustive cycle exercise. In addition, the serum insulin and glucose responses among the three eucaloric feedings displayed no differences at any time throughout the 4-hour restoration period.

Insulin is also necessary for the uptake of amino acids to tissues and for protein synthesis. Proteins are the compounds comprised of amino acids and are the building blocks of tissue formation within the body. The synthesis of protein is the method by which muscles are constructed. The human body synthesizes protein from diet at a rapid rate while the body is growing through adolescence and into young adulthood. The rate at which protein is synthesized slows significantly after age 20. In fact between the age of 20 and 80 humans lose approximately 20-30% of their skeletal muscle mass.

This age-related loss of muscle mass is often referred to as "sarcopenia of old age" and is the consequence of complicated a multifactorial processes or disorders. A variety of intrinsic and extrinsic factors appear to be involved in the aging skeletal muscle. Changes in intrinsic factors associated with aging muscle include hormone, growth factor and systems associated with energy such as glucose or fatty acid metabolism, whereas intrinsic factors include diet, exercise, injuries and sedentary lifestyle.

Hence, there may be a correlation between the glucose metabolism and the synthesis of proteins so that an improvement of the rate of re-synthesis of muscle glycogen also may show a beneficial effect on the rate of protein synthesis in the muscles. In fact impairment of insulin action on muscle glycogen storage may play an important role in general on age-related changes in muscle mass. The muscle glycogen synthesis pathway is often found to be impaired with type 2 diabetes. Decreased insulin action with aging may be related to decrease in lean body mass and/or to the impaired ability of the muscle to respond to insulin (Carmeli et al.).

Fujita et al. investigated how aerobic exercise affects the anabolic response of skeletal muscle protein synthesis to insulin in healthy older subjects. The result of their research showed that a single bout of moderate aerobic exercise overcomes the muscle protein insulin resistance and restores the physiological anabolic response of muscle protein synthesis to insulin in older people. More specifically they showed that muscle protein synthesis significant increased during insulin infusion only if the infusion was preceded by a bout of aerobic exercise. The effect was directly associated with an increase in blood flow which in turn was accompanied by a significant increase in amino acid delivery and transport into muscle tissue.

*Stevia rebaudiana* Bertoni (SrB) is a shrub native to Brazil and Paraguay. The leaves from this plant contain a large amount of the steviol glycoside, stevioside, which is a non-caloric sweetener 300 times sweeter than sucrose. Extracts from *Stevia rebaudiana* have been used for many years in South America in the treatment of diabetes indicating that compounds in the extract may affect the glucose metabolism in a beneficial way.

Lailerd et al. have studied the effect of stevioside treatment on skeletal muscle glucose transport activity in both insulin-sensitive lean (Fa/−) and insulin-resistant obese (fa/fa) Zucker rats. In the study the rats were restricted to 4 g of chow two hours before start of the test. At the start of the test the rats were administered either 200 or 500 mg/kg body weight stevioside by gavage. Two hours later the rats were given a 1 g/kg body weight glucose load by gavage. Blood samples were then collected at 0, 15, 30, 60 and 120 minutes after glucose feeding. Their results showed that the acute oral administration of stevioside did not significantly affect fasting plasma glucose and insulin. Also the in vitro glucose transport activity in skeletal muscle was investigated. In this experiment one soleus and both epitrochlearis muscles were dissected and incubated with a stevioside-containing solution. The result of this experiments indicated that stevioside improves the insulin action on skeletal muscle glucose transport system in both insulin-sensitive lean and insulin-resistant obese Zucker rats in dose-dependent fashion. It was not possible, however, to determine whether the concentrations of stevioside that were effective in positively modulating in vitro glucose transport in insolated skeletal muscle can be achieved in vivo following oral administration of the compound.

Gregersen et al. (2004) have studied the acute effects of stevioside in type 2 diabetic patients. In the study the patients were given a standard meal supplemented with either 1 g of stevioside or 1 g of maize starch (control). The results of their study showed that stevioside suppresses the postprandial blood glucose level in type 2 diabetic subjects in average 18% and the circulating insulin levels tended to be increased by stevioside. The article mentions the author's earlier in vitro studies in isolated mouse islets, which showed a glucose-dependent insulin release to stevioside, whereas the insulinotropic effect of stevioside faded in the presence of normal to low glucose. It is therefore hypothesized that an elevated glucose level, as found in the diabetic state, is needed for stevioside to elicit its beneficial effects.

In another study Gregersen et al. (2006) investigated whether the combination of stevioside and soy bean protein isolate would show an improvement in the treatment of diabetes in Goto-Kakizaki rats. In the study adult male GK weighing 200-300 g at the age of 20 weeks were divided into four groups and fed for 4 weeks with different pellet diets: Group 1 received a standard carbohydrate-rich laboratory diet (chow), group 2 received chow+stevioside (0.03 g/kg body weight), group C received 80% soya bean protein+ 20% chow, and group 4 received 80% soya bean protein+ stevioside (0.03 g/kg body weight). The results of this study revealed that the combination of stevioside and soy bean protein isolate has synergistic positive effects on the characteristic features of the metabolic syndrome, i.e. hyperglycemia, hypertension and dyslipidemia.

International patent application WO 2006/116814 describes a composition used to treat hyperglycaemia and associated conditions. In particular, the document discloses a composition comprising an extract from at least one plant from the genus Stevia and at least one bile salt. In the experimental part of the document adult Wistar rats are treated with stevioside, 20 mg/kg, orally, daily for 5 days. Both a group of non-diabetic rats and a group of diabetic rats were tested. 15 minutes after the 5$^{th}$ dose, the animals were exposed to an oral glucose tolerance test using 4 g/kg, orally. Glucose blood concentrations were measured before the treatment, after the 5$^{th}$ dose, before the glucose test and 30 minutes after the glucose test. It is concluded that treatment with stevioside alone (i.e. when not co-administered with the bile salt) conferred beneficial effects on glucose levels under increased loading during the glucose test. However, no significant decrease in glucose levels was seen before the glucose test (i.e. before administration of glucose) when compared to the control group. These results support the finding that stevioside shows a blood glucose decreasing effect only in cases where the blood glucose level is higher than the normal level.

International patent application WO 01/56959 is directed to a substance for use in a dietary supplementation or for preparation of a medicament for the treatment of non-insulin dependent diabetes mellitus, hypertension and/or the metabolic syndrome. Stevioside is mentioned as a preferred example of such a substance. In one of the experiments type II diabetic patients are given a standard meal supplemented with 1 g of stevioside orally. Blood samples were collected 4 hours later. The results show that stevioside reduced the post prandial blood glucose response by 18.5% compared to placebo and tended to stimulate insulin response in type II diabetic patients, even though the difference did not reach statistical significant level. The results further showed that stevioside significantly reduced the postprandial glycogen level and the postprandial glucagon like peptide-1 level.

In yet another study it has been shown that steviol glycosides inhibit 11β-hydroxysteroid dehydrogenase type 1 (Diabetes, Obesity and Metabolism. 10 (10): 939-49, 2008). 11β-hydroxysteroid dehydrogenase type 1 is the name of a family of enzymes that catalyze the conversion of inert 11 keto-products (cortisone) to active cortisol, or vice versa, thus regulating the access of glucocorticoids to steroid receptors. An increased production of cortisol may result in an increased insulin resistance.

It has not previously been reported whether the intake of stevioside, or any related compound such as steviol or a steviol glycoside, affect the muscle glycogen re-synthesis in human beings, whose muscles are depleted of glycogen due to for instance exhaustive exercise. Neither has it been reported whether the intake of stevioside, or any related compound such as steviol or a steviol glycoside, affect the muscle protein synthesis in human beings, whose muscles are depleted in protein mass due to lack of exercise.

The present inventors have surprisingly found a beneficial effect of stevioside intake on muscle glycogen depletion and loss of muscle mass. None of the published studies have provided any information indicating that stevioside or related compounds would beneficially affect healthy subjects. Such finding could indicate that another mechanism exists in addition to the known beneficial effect on insulin sensitivity seen only for diabetes type 2 subjects.

SUMMARY OF INVENTION

The present invention broadly relates to steviol glycoside for use in treating deteriorating effects in muscles, such as muscle glycogen depletion and loss of muscle mass, which may result from excessive training.

Accordingly, the present invention is directed to a composition comprising a steviol glycoside for use in the treatment of muscle glycogen depletion and/or for use in the treatment of loss of muscle mass in a human being by oral administration of said composition, wherein said steviol glycoside is selected from the group consisting of rebaudioside A, rebaudioside B, rebaudioside C, rebaudioside D, rebaudioside E, rebaudioside F, dulcoside A, steviol, isosteviol, stevioside, steviolbioside, rubusoside, and mixtures thereof. Preferably, the steviol glycoside is stevioside. The compositions may be formulated as solid, frozen, semi-solid or liquid compositions.

DETAILED DESCRIPTION OF THE INVENTION

Figure 1:
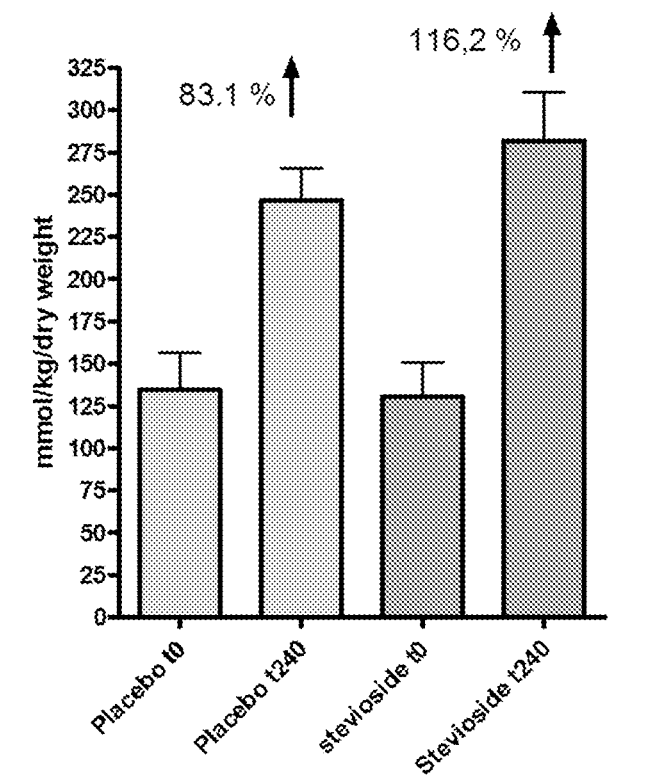
FIG. 1. Glycogen concentration and glycogen synthesis rate for stevioside supplementation compared to placebo supplementation.
Figure 1:
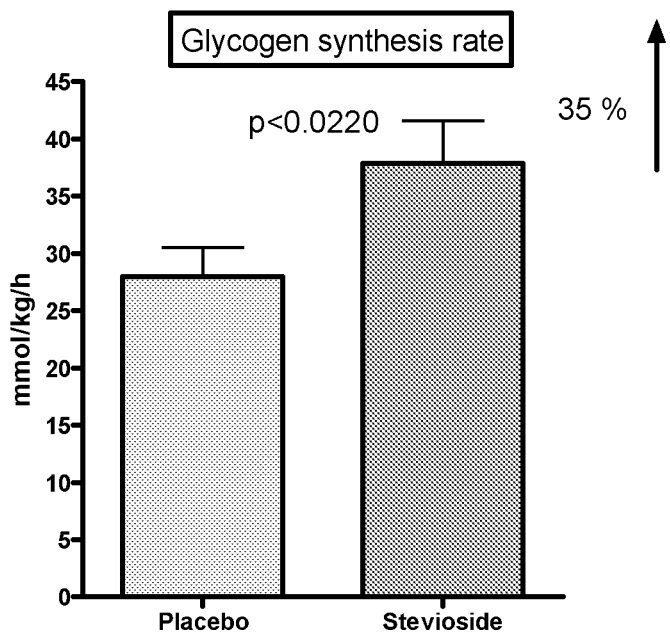

The compositions of the present invention comprise a steviol glycoside. Preferably, the compositions of the present invention also comprise carbohydrate, protein and/or electrolytes. Additionally the compositions may also comprise further ingredients.

The compositions may be formulated as solid, frozen, semi-solid or liquid compositions.

Steviol Glycoside(s)

The compositions of the present invention comprises a steviol glycoside and/or an aglycone thereof, which act as the active compound by increasing the rate of glycogen re-synthesis in muscles that are depleted in glycogen due to exhaustive exercise and/or by increasing the rate of protein synthesis in muscles that are depleted in protein muscle mass.

Non-limiting examples of steviol glycosides and aglycones thereof that are suitable for use in the compositions of the present invention include rebaudioside A, rebaudioside B, rebaudioside C, rebaudioside D, rebaudioside E, rebaudioside F, dulcoside A, steviol, isosteviol, stevioside, steviolbioside, rubusoside, and combinations thereof. For example, steviol and isosteviol are aglycones of steviol glycoside.

The general structure of steviol and its related glycosides are provided below. Glc, Xyl and Rha represent glucose, xylose and rhamnose sugar moieties, respectively.

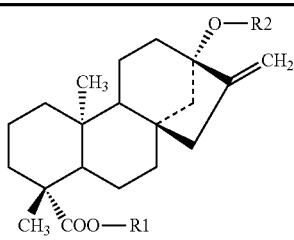

| Compound name | C.A.S. No. | R1 | R2 |
|---|---|---|---|
| 1 Steviol | 471-80-7 | H | H |
| 2 Steviolbioside | 41093-60-1 | H | β-Glc-β-Glc(2→1) |
| 3 Stevioside | 57817-89-7 | β-Glc | β-Glc-β-Glc(2→1) |
| 4 Rebaudioside A | 58543-16-2 | β-Glc | β-Glc-β-Glc(2→1)<br>\|<br>β-Glc(3→1) |

-continued

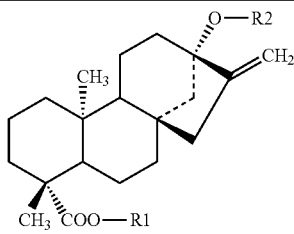

| Compound name | C.A.S. No. | R1 | R2 |
|---|---|---|---|
| 5 Rebaudioside B | 58543-17-2 | H | β-Glc-β-Glc(2→1)<br>\|<br>β-Glc(3→1) |
| 6 Rebaudioside C (dulcoside B) | 63550-99-2 | β-Glc | β-Glc-α-Rha(2→1)<br>\|<br>β-Glc(3→1) |
| 7 Rebaudioside D | 63279-13-0 | β-Glc-β-Glc(2→1) | β-Glc-β-Glc(2→1)<br>\|<br>β-Glc(3→1) |
| 8 Rebaudioside E | 63279-14-1 | β-Glc-β-Glc(2→1) | β-Glc-β-Glc(2→1) |
| 9 Rebaudioside F | 438045-89-7 | β-Glc | β-Glc-β-Xyl(2→1)<br>\|<br>β-Glc(3→1) |
| 10 Rubusoside | 63849-39-4 | β-Glc | β-Glc |
| 11 dulcoside A | 64432-06-0 | β-Glc | β-Glc-β-Rha(2→1) |

The preferred steviol glycoside is stevioside.

The steviol glycoside or its aglycone, such as steviol or isosteviol, is preferably present in the compositions in an amount of 50 mg to 1000 mg, such as for example 100 mg to 900 mg, such as for example 250 mg to 750 mg, such as for example 400 mg to 600 mg, preferably 500 mg.

Preferably the steviol glycoside is stevioside and preferably the amount of stevioside in the composition lies in the range of 50 mg to 1000 mg, such as for example 100 mg to 900 mg, such as for example 250 mg to 750 mg, such as for example 400 mg to 600 mg, preferably 500 mg.

In another preferred embodiment, the provided composition comprises an aglycone of a steviol glycoside, such as isosteviol and/or steviol, in the range of 50 mg to 1000 mg, such as for example 100 mg to 900 mg, such as for example 250 mg to 750 mg, such as for example 400 mg to 600 mg, preferably 500 mg.

Carbohydrate

The composition of the present invention must preferably comprise at least one carbohydrate in order to provide glucose to be stored in the glycogen-depleted muscles. The term "carbohydrate" as used herein refers to aldehyde or ketone compounds substituted with multiple hydroxyl groups of the general formula $(CH_2O)_n$, wherein n is 3-30, as well as oligomers and polymers. The carbohydrates of the present invention can in addition be substituted or deoxygenated at one or more positions.

Non-limiting examples of carbohydrates include tagatose, trehalose, galactose, rhamnose, cyclodextrin (e.g. α-cyclodextrin, β-cyclodextrin and γ-cyclodextrin), maltodextrin (including resistant maltodextrins such as Fibersol), dextran, sucrose, glucose, ribulose, fructose, threose, arabinose, xylose, lyxose, allose, altrose, mannose, idose, lactose, maltose, invert sugar, isotrehalose, neotrehalose, palatinose or isomaltulose, leucrose, erythrose, deoxyribose, gulose, idose, talose, erythrulose, xylulose, psicose, turanose, cellobiose, amylopectin, glucosamine, mannosamine, fucose, glucuronic acid, gluconic acid, glucono-lactone, abequose, galactosamine, beet oligosaccharides, isomalto-oligosaccharides (isomaltose, isomaltotriose, panose and the like), xylo-oligosaccharides (xylotriose, xylobiose and the like), gentio-oligosaccharides (gentiobiose, gentiotriose, gentiotetraose and the like), sorbose, nigero-oligosaccharides, fucose, palatinose oligosaccharides, fructooligosaccharides (kestose, nystose and the like), maltotetraol, maltotriol, malto-oligosaccharides (maltotriose, maltotetraose, maltopentaose, maltohexaose, maltoheptaose and the like), lactulose, melibiose, raffinose, rhamnose, ribose, isomerized liquid sugars such as high fructose corn/starch syrup (e.g., HFCS55, HFCS42 or HFCS90), coupling sugars, soybean oligosaccharides or glycose syrup.

The preferred carbohydrate is maltodextrin. Maltodextrin is an oligosaccharide that is used as a food additive. Maltodextrin consists of D-glucose units connected in chains of variable length. The glucose units are primarily linked with $\alpha(1\to4)$ glycosidic bonds. Maltodextrin is typically composed of a mixture of chains that vary from three to seventeen glucose units long. It is produced from starch, such as barley, wheat, and potato, by partial hydrolysis and is usually found as a white hygroscopic spray-dried powder. Maltodextrin is easily digestible, being absorbed as rapidly as glucose, and might be either moderately sweet or almost flavorless. It is commonly used for the production of sodas and candy. It can also be found as an ingredient in a variety of other processed foods.

The carbohydrate is preferably present in the compositions in an amount of 20 to 150 g, such as for example 50 to 100 g. When the carbohydrate is maltodextrin, it is preferably present in the compositions in an amount of 20 to 150 g, such as for example 50 to 100 g.

Polyol additives may also be included in the compositions of the present invention as sweet taste improving additives. Polyols are also known as sugar alcohols. The term "polyol" and "sugar alcohols" as used herein refers to the hydrogenated form of carbohydrate.

Non-limiting examples of polyol additives include erythritol, maltitol, mannitol, sorbitol, lactitol, xylitol, inositol, isomalt, propylene glycol, glycerol (glycerine), threitol, galactitol, palatinose, reduced isomalto-oligosaccharides, reduced xylo-oligosaccharides, reduced gentio-oligosaccharides, reduced maltose syrup and reduced glucose syrup.

The composition of the present invention may also comprise a sweet taste improving sugar acid additive. Non-limiting examples of such sugar acid additives include aldonic, uronic, aldaric, alginic, gluconic, glucuronic, glucaric, galactaric, galacturonic or salts thereof (e.g. sodium, potassium, calcium, magnesium salt or other physiologically acceptable salts) and combinations thereof.

Protein

The compositions of the present invention also preferably comprise a protein source. The term "protein source" as used herein refers to amino acids, peptides, natural protein sources and combinations thereof.

The protein source may also be in the form of amino acids. By the term "amino acid" as used herein refers to organic compounds comprising both —NH$_2$ and —COOH groups. Non-limiting examples of amino acids include aspartic acid, arginine, glycine, glutamic acid, proline, threonine, theanine, cysteine, cystine, alanine, phenylalanine, valine, tyrosine, tryptophane, leucine, isoleucine, asparagine, serine, lysine, histidine, ornithine, methionine, carnitine, creatine, glucuronolactone, inositol, aminobutyric acid (alpha-, beta-, and gamma-isomers), glutamine, hydroxyproline, taurine, norvaline, sarcosine and their salt forms such as sodium or potassium salts or acid salts. The amino acids may be in their D- or L-configuration. Additional the amino acids may be in their $\alpha$-, $\beta$-, $\gamma$-, $\delta$- and $\epsilon$-isomers if appropriate. The amino acids may be natural or synthetic. The amino acids may also be modified, wherein at least one atom has been added, removed or substituted, e.g. N-alkyl amino acid, N-acyl amino acid or N-methyl amino acid. Non-limiting examples of modified amino acids include trimethyl glycine, N-methyl-glycine and N-methyl-alanine.

The protein source may be in the form of peptides, such as dipeptides, tripeptides, tetrapeptides, pentapeptides etc, such as for example glutathione and L-alanyl-L-glutamine. An important peptide source include spray-dried combination of casein hydrolysate and malic acid, known as Pepto-Pro (DSM), which is a protein hydrolysates derived from casein protein fraction of cow's milk.

The protein source may also be in the form of vegetable proteins. The vegetable proteins may be present either in their native state or as hydrolysates. Non-limiting examples of vegetable proteins include soya protein, soya protein isolate, soy protein concentrate, pea protein, rice protein, soy flour, wheat protein, whey protein, corn protein, nut protein or a combination comprising at least one of the foregoing proteins.

In a preferred embodiment the protein source is whey protein.

Whey protein is the collection of globular proteins isolated from whey, a by-product of cheese manufactured from cow's milk. The protein in cow's milk is 20% whey protein and 80% casein protein, whereas the protein in human milk is 60% whey and 40% casein. Whey protein is typically a mixture of beta-lactoglobulin (~65%), alpha-lactalbumin (~25%), and serum albumin (~8%), which are soluble in their native forms, independent of pH. The protein fraction in whey (approximately 10% of the total dry solids within whey) comprises four major protein fractions and six minor protein fractions. The major protein fractions in whey are beta-lactoglobulin, alpha-lactalbumin, bovin serum albumin and immunoglobulins. Whey protein typically comes in three major forms: concentrate (WPC), isolate (WPI), and hydrolysate (WPH). Concentrates have typically a low (but still significant) level of fat and cholesterol but, in general, higher levels of bioactive compounds, and carbohydrates in the form of lactose. Isolates are processed to remove the fat, and lactose, but are usually lower in bioactivated compounds as well. Like whey protein concentrates, whey protein isolates are mild to slightly milky in taste. Hydrolysates are whey proteins that are predigested and partially hydrolyzed for the purpose of easier metabolizing, but their cost is generally higher. Highly-hydrolysed whey may be less allergenic than other forms of whey. The isolate (WPI) is suitable used in compositions prepared for human beings who need to restore their muscle glycogen that are depleted in glycogen due to exhaustive exercise. Hydrolysate (WPH) is suitable used in composition prepared for human beings, who need to restore muscle mass by increasing the rate of protein synthesis.

Other non-limiting examples of proteins sources that can be included in the compositions of the present invention include bovine serum albumin, egg albumin, yeast concentrate or a combination comprising at least one of the foregoing proteins.

The protein source is generally present in the composition in an amount of about 15 g to 150 g.

The compositions of the present invention may also comprise sweet taste improving nucleotide additives. Non-limiting examples of such nucleotide additives include inosine monophosphate ("IMP"), guanosine monophosphate ("GMP"), adenosine monophosphate ("AMP"), cytosine monophosphate ("CMP"), uracil monophosphate ("UMP"), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate and their alkali or alkaline earth metal salts and combinations thereof.

Electrolytes

The compositions of the present invention also preferably comprise electrolytes. Sodium, potassium, magnesium, calcium and chloride are some of the more important electrolytes/minerals that are involved in filling body fluid compartments. It is further believed that electrolytes and minerals play an important role in rehydration by possibly affecting fluid replacement and fluid retention. In response to fluid loss during dehydration, water is distributed between fluid compartments so that both the extracellular and intracellular compartments share the water deficit.

Non-limiting examples of sodium compounds include sodium chloride, sodium acetate, acidic sodium citrate, acidic sodium phosphate, sodium bicarbonate, sodium bromide, sodium citrate, sodium lactate, sodium phosphate, sodium pyruvate, anhydrous sodium sulphate, sodium sulphate, sodium tartrate, sodium benzoate and sodium selenite.

Non-limiting examples of potassium compounds include potassium chloride, potassium acetate, potassium bicarbonate, potassium bromide, potassium citrate, potassium-D-gluconate, potassium monophosphate, potassium diphosphate, potassium tartrate, potassium sorbate and potassium iodide. Potassium monophosphate is the preferred potassium compound.

Non-limiting examples of magnesium compounds include magnesium acetate, magnesium chloride, magnesium diphosphate, magnesium triphosphate, magnesium oxide, magnesium sulphate, magnesium carbonate, magnesium aspartate and magnesium silicate. Magnesium oxide is the preferred magnesium compound.

Non-limiting examples of chloride compounds include sodium chloride, potassium chloride, magnesium chloride and mixtures thereof. Sodium chloride preferred.

Calcium may also be present in the composition. Non-limiting examples of calcium compounds include calcium lactate, calcium carbonate, calcium chloride, calcium phosphate salts, calcium citrate. Calcium lactate is the preferred calcium compound.

Electrolytes are generally present in the composition in an amount of 1 to 300 mmol/l Other Ingredients The compositions of the present invention may further comprise other ingredients such as food-grade organic acids, food-grade inorganic acids, bitter compound additives, flavour additives, taste improving polymer additives, emulsifier additives, thickening additives, preservatives, comprise vitamins or vitamin precursors, minerals, micronutrients, phytochemicals, stimulants, cognitive enhancing additives and relaxants.

The compositions of the present invention may also comprise food-grade organic acids. Non-limiting examples of suitable food-grade organic acids for use in the compositions include acetic acid, adipic acid, alginic acid, ascorbic acid, benzoic acid, bile acids, butyric acid, caffeic acid, chlorogenic acid, citric acid, erythorbic acid, formic acid, fruitaric acid (a blend of malic, fumaric and tartaric acids), fumaric acid, glyconic acid, glucoheptonic acid, hydroxycitric acid, lactic acid, maleic acid, malic acid, phosphoric acid, polyglutamic acid, oxalic acid, salicylic acid, succinic acid, tannic acid, tartaric acid and combinations thereof. The food-grade acids can be added as acidulant to control the pH of the composition and also to provide preservative properties or to stabilise the composition. Compositions of the present invention preferably have a pH of from about 2.5 to about 6.5, preferably 2.5 to 4.5, more preferably 3 to 4. In addition citric acid and the like add tartness to the beverage.

The compositions of the present invention may also comprise food-grade inorganic acids. Non-limiting examples of suitable food-grade inorganic acids for use in the compositions include phosphoric acid, phosphorous acid, polyphosphoric acid, hydrochloric acid, sulphuric acid, carbonic acid, sodium dihydrogen phosphate and combinations thereof.

The compositions of the present invention may also comprise bitter compound additives. Non-limiting examples of suitable bitter compound additive include caffeine, quinine, urea, orange oil, naringin, quassia, salts thereof and any combinations thereof.

The compositions of the present invention may also comprise flavour additives. The use of flavour additives is to provide an enhanced aesthetic quality to the nutritional composition, which will increase the user's appeal in using the product. The flavour additives may be water soluble natural or artificial additives. Non-limiting examples of suitable flavour additives include almond, apple, banana, cherry, chocolate, cinnamon, citrus, coconut, cola, cranberry, ginger, grape, honeydew, honey, kiwi, lemon, lime, mango, menthol, orange, peach, peppermint, pineapple, raspberry, tangerine, vanilla, viridiflorol, watermelon, wild cherry and equivalents and combinations thereof.

The compositions of the present invention may also comprise taste improving polymer additives. Non-limiting examples of such taste improving polymer additives include chitosan, pectin, pectic acid, pectinic acid, polyuronic acid, polygalacturonic acid, starch, food hydrocolloid or crude extracts thereof (e.g., gum acacia Senegal, gum acacia seyal, carrageenan), poly-L-lysine, poly-L-ornithine, polyarginine, polypropylene glycol, polyethylene glycol, poly(ethylene glycol methyl ether), polyaspartic acid, polyglutamic acid, poly ethyleneimine, alginic acid, sodium alginate, propylene glycol alginate, sodium hexametaphosphate and its salts or other cationic and anionic polymers.

The semi-solid and liquid compositions of the present invention may also comprise emulsifier additives in order to prevent separation of the composition components by keeping the ingredients dispersed. Emulsifier additives include molecules which have both a hydrophilic part and a hydrophobic part. Emulsifier additives operate at the interface between hydrophilic and hydrophobic materials of the semi-solid or liquid composition to prevent separation of the components of the composition. Non-limiting examples of suitable emulsifier additives for use in the compositions include lecithin (e.g. soy lecithin); mono and di-glycerides of long chain fatty acids, specifically saturated fatty acids, and more specifically, stearic and palmitic acid mono- and diglycerides; mono- and di-glycerides of acetic acid, citric acid, tartaric acid or lactic acid, egg yolks; polysorbates (e.g., polysorbate 20, polysorbate 40, polysorbate 60, polysorbate 65 and polysorbate 80), propylene glycol esters (e.g. propylene glycol monostearate); propylene glycol esters of fatty acids, sorbitan esters (e.g. sorbitan monostearates, sorbitan tristearates, sorbitan monolaurate, sorbitan monooleate), Acacia (gum Arabic), sucrose monoesters; polyglycerol esters; polyethoxylated glycerols; and combinations thereof. Compositions of the present invention may also comprise omega-3 and/or omega-6 fatty acids.

The compositions of the present invention may also comprise thickening additives. Thickening additives which can impart added "mouth-feel" to the composition include natural and synthetic gums for example locust bean gum, guar gum, gellan gum, xanthan gum, gum ghatti, modified gum ghatti, tragacanth gum, carrageenan and the like; natural and modified starches, for example pregelatinized starch (corn, wheat, tapioca), pregelatinized high amylose-content starch, pregelatinized hydrolysed starches (maltodextrins, corn syrup solids), chemically modified starches such as pregelatinized substituted starches (e.g. octenyl succinate), and the like; cellulose derivatives for example carboxymethylcellulose, sodium carboxymethylcellulose and the like, polydextrose; whey or whey protein concentrate; pectin; gelatin and a combination thereof.

The compositions of the present invention may also comprise preservatives. Such preservatives can be added to the composition to provide freshness and to prevent the unwanted growth of bacteria, moulds, fungi or yeast. The addition of preservatives, including antioxidants, may also be used to maintain the composition's colour, flavour or texture. Any suitable preservatives for use in food and beverage products can be incorporated into the compositions. Examples include benzoic acid alkali metal salts (e.g. sodium benzoate), sorbic acid alkali metal salts (e.g. potassium sorbate), ascorbic acid (Vitamin C), citric acid, calcium propionate, sodium erythorbate, sodium nitrite, calcium sorbate, butylated hydroxyanisole (BHA), butylated hydroxytoluene (BHT), ethylenediaminetetraacetic acid (EDTA), tocopherols (Vitamin E), di-alpha-tocopheryl phosphate, tocotrienols, alpha lipoic acid, dihydrolipoic acid, straight chain polyphosphates and combinations thereof. The compositions may also comprise natural preservatives, which include rosemary extracts comprising carnosic, rosemarinic and ursolic acid. Preservatives also include well-known antioxidants such as for example polyphenols (preferably cocoa), xanthophylls, beta cryptoxanthin, lycopene lutein, zeaxanthin, astaxanthin, beta-carotene, carotenes, mixed carotenoids, resveratrol, flavonoids and combinations thereof.

The compositions of the present invention may also comprise vitamins or vitamin precursors. Non-limiting suitable examples of such vitamin or vitamin precursors include ascorbic acid (Vitamin C), beta carotene, niacin (Vitamin B3), riboflavin (Vitamin B2), thiamine (Vitamin B1), niacinamide, folate or folic acid, alpha tocopherols or esters thereof, Vitamin D, retinyl actate, retinylpalmitate, pyridoxine (Vitamin B6), folic acid (Vitamin B9), cyanocobalimin (Vitamin B12), pantothenic acid, biotin and combinations thereof. Some of the vitamins are fat soluble such as vitamin A, vitamin D, vitamin E and vitamin K, whereas other of the vitamins are water soluble, such as vitamin C (ascorbic acid), the B vitamins (thiamine or B1, riboflavin or B2, niacin or B3, pyridoxine or B6, folic acid or B9, cyanocobalamin or B1, pantothenic acid, biotin.

The compositions of the present invention may also comprise minerals. Non-limiting suitable examples of minerals include iron, zinc, chromium, calcium, copper and magnesium.

The compositions of the present invention may also comprise micronutrients. Non-limiting examples of such micronutrients include L-carnitine, choline, coenzyme Q10, alpha-lipoic acid, omega-3-fatty acids (preferably long chain polyunsaturated fatty acids), pepsin, phytase, trypsin, lipases, proteases, lactotripeptide, Isoleucine-Proline-Proline (IPP), cellulases and combinations thereof.

The compositions of the present invention may also comprise phytochemicals (phytonutrients). Phytochemicals are plant derived compounds which may provide a beneficial effect on the health or well-being of the consumer. Phytochemicals include plant derived antioxidants, phenolic compounds including monophenols and polyphenols and the like. Non-limiting examples of such phytochemicals include lutein, lycopene, carotene, anthocyanin, capsaicinoids, flavonoids hydroxycinnamic acids, isoflavonols, isothiocyanates, monoterpenes, chalcones, coumestans, dihydroflavonols, flavonoids, flavanols, quercetin, flavanones, flavones, flavan-3-ols (catechins, epicatochin, epigallocatechin, epigallocatechingallate and the like), flavonals (anthocyanins, cyanidine and the like); phenolic acids, phytosterols, saponins, terpenes (carotenoids) and combinations thereof.

The compositions may further include one or more stimulants in order to reduce physical and mental impairment of the human being during and following exercise. Non-limiting examples of suitable stimulants include taurine, caffeine and green tea and combinations thereof.

The compositions of the present invention may also comprise cognitive enhancing additives. Non-limiting examples of such cognitive enhancing additives include green tea extracts, L-theanine, phosphatidyl serine, acetyl carnitine, CDP-choline and combinations thereof.

The compositions of the present invention may also comprise relaxants such as melatonin.

Formulation of the Compositions

The compositions of the present invention may be formulated as solid, frozen, semi-solid and liquid compositions.

The composition of the present invention must comprise at least one steviol glycoside and preferably at least one carbohydrate in order to provide glucose to be stored in the glycogen-depleted muscles.

In alternative embodiments of the present invention the composition does not comprise a carbohydrate. In such cases it is necessary to administer the composition comprising steviol glycoside together with another composition comprising carbohydrate. Such embodiments where the steviol glycoside composition and the carbohydrate composition is stored and sold separately the human being to be treated is free to combine the compositions so that an optimal combination of steviol glycoside and carbohydrate is obtained. Hence, different amount and mixtures of steviol glycosides may be combined with different amounts, types and mixtures of carbohydrates.

Solid compositions include, but are not limited to, chocolate and nutritional bars, drops, candies, cookies, cereals, snack bars and biscuits. Solid compositions also include tablets, sachets, capsules, powders and concentrates to be reconstituted before use by addition of water or an appropriate liquid.

Frozen compositions include, but are not limited to, frozen desserts, ice creams, ice sherbets and ice shavings.

Semi-solid compositions include, but are not limited to, cream, jam and gels, yoghurt, pudding and jelly.

Liquid compositions include ready-to drink compositions and concentrates to be reconstituted before use by addition of water or an appropriate liquid. Suitable examples of liquid compositions include, but are not limited to, sports drinks, beverages, refreshing beverages, carbonated water, flavoured water, carbonated flavoured water, drinks containing juice (juice derived from any fruit or any combination of fruits, juice derived from ant vegetable or any combination of vegetables) or nectar, vitamin enhanced sports drinks, high electrolyte sport drinks highly caffeinated high energy drinks, coffee, decaffeinated coffee, tea, tea from fruit products, tea derived from herb products decaffeinated tea, milk obtained from animals, milk products derived from soy, rice, coconut or other plant material, fermented milk products and drinking chocolates.

Human Beings to be Treated

In some aspects, human beings to be treated by the compositions according to the present invention include any human being in need of restoring their muscle glycogen content. The depletion of muscle glycogen may be caused by physical activity of the human being. By the term "physical activity" as used herein is meant vigorous exercise and in particular physical exercise for a period that results in exhaustion. Suitable forms of exercise include running, football, rugby, cycling, jogging, biathlons, triathlons, marathons, tennis, basketball, squash, housework, dancing and the like. Preferably the duration of the exercise is at least 20 minutes, more preferably 30 minutes or more.

In some embodiments the human beings are athletes, such as endurance and team sports athletes as well as athletes participating in weight class regulated sports, such as for example professional cyclists and professional football player and ice hockey players. In particular during competitions that continue for more than one day, such as for example Tour de France and the World Championship in Football or Ice Hockey, where the players are competing every day or almost every day, it is important that the restoration of muscle glycogen is optimized and that the rate of re-synthesise of muscle glycogen is proceedings as fast as possible.

In some aspects, human beings to be treated also include elderly people, whose muscles are depleted in protein muscle mass due to lack of exercise. It is known that aging is associated with a loss of muscle mass, at a rate of 1% per year, after the age of 50. This loss in muscle mass often results in a loss of independence in elderly, together with an increased risk of falling and premature death. Also elderly people who in a period has been ill in bed or has been bedridden because of surgery may take advantage of oral intake of the compositions of the present invention during their period of rehabilitation, because their depleted muscle mass may be restored during a shorter period of time and thereby improving the elderly's mobility, activity and well-being.

In some embodiments the group of human beings to be treated includes all healthy and non-healthy human beings. In some embodiments, the group of human beings to be treated does not include subjects suffering of diabetes type 2. In some embodiments, the group of human beings to be treated does not include subjects suffering of type 2 diabetes or metabolic syndrome. In other embodiments the group of human beings to be treated does not include subjects suffering of insulin resistance.

In some embodiments, the group of human beings to be treated includes subjects in need of treatment of muscle glycogen depletion due to exhaustive exercise. Examples of such human beings include athletes, such as endurance and team sports athletes as well as athletes participating in weight class regulated sports. Other examples include professional cyclists and professional football player and ice hockey players.

In some embodiments, the group of human beings to be treated includes subjects in need of treatment of loss of muscle mass. Examples of such human beings include elderly people. Other examples include elderly people, who have been bedbound for a period due to illness or surgery. Other examples include elderly people, who have not been physical active for a period. In yet other embodiments, the group of human beings to be treated includes subjects of all ages during their period of rehabilitation. In other embodiments the group to be treated includes elderly people during their period of rehabilitation.

Administration Regime

The composition of the present invention may be taken prior to and/or during and/or after an exercise.

The daily dosage of steviol glycoside, or its aglycone, such as steviol or isosteviol, lies in the range of 50 to 2000 mg, such as for example 500 to 1500 mg, such as for example 900 to 1100 mg, such as for example 1000 mg.

The daily dosage of carbohydrate, such as maltodextrin, lies in the range of 5 to 500 g/day, such as for example 10 to 250 g/day, such as for example 20 to 150 g/day.

The daily dosage of protein, such as whey protein, lies in the range of 5 to 500 g/day, such as for example 10 to 250 g/day, such as for example 15 to 150 g/day.

EXAMPLES

The examples herein will serve to test if stevioside possess a beneficial effect with regard to the rate of resynthesis of glycogen, and demonstrate a positive effect of stevioside on the rate of resynthesis of glycogen.

Example 1

Effect of Stevioside Intake During Physical Activity on Time of Exhaustion

The aim of this experiment is to investigate if intake of stevioside in addition to a carbohydrate-containing composition during exhaustive bicycling work will prolong the period of time before exhaustion as compared with intake of the carbohydrate-containing composition alone.

Test Subjects 15-20 healthy and well trained male subjects will be selected for the study. The subjects will be completing the test procedure twice, on two separate days at least 7 days apart in a crossover design, where intervention—i.e. the additional intake of stevioside together with the carbohydrate-containing composition during the bicycling work—is blinded and randomised for both the test subjects and the scientific staff.

Inclusion Criteria:

Well trained, healthy exhaustive trained males, age 18 to 40, having a maximal oxygen uptake (VO2-max) of at least 55 ml $O_2$ per kg body weight per minute.

Exclusion Criteria:

Persons suffering of a metabolic disease, which is related to the carbohydrate metabolism, such as diabetes type 1 or 2, insulin resistance and the like, cannot be included in the test. Also persons, who are prescribed a medical drug or diet supplement that could affect the carbohydrate metabolism, will be excluded from the study. Finally persons that are not capable of completing the fasting period or the test protocol will be excluded from the study.

Before Testing

Before testing the VO2-max and the Watt-max will be determined for each test person. The test will be performed on a bicycle ergometer as a "step test" where the workload will be increased with 20 watt every 60 seconds, while the test person will be exercising continuous bicycling work. The test will be discontinued when the test subject experiences exhaustion. VO2 will be measured every 15 seconds. A discharge of intake of oxygen despite an increasing working load and a respiratory coefficient (RER)≥1.15 will be taken as the criterion for obtainment of maximum VO2.

The test will be performed at least 72 hours before the first duration-before-exhaustion-test (DBET).

Experimental Design:

The test persons will be completing the test twice on two separate days at least 7 days apart in a crossover design, where the intervention—i.e. the additional intake of stevioside together with the carbohydrate-containing composition during the bicycling work—is blinded and randomised for both the test subjects and the scientific staff.

The test will start by a starving period of 12 hours. Thereafter the test will commence by a 5 minutes warming-up period corresponding to 50% watt-max workload and then the test person will pedal for 120 minutes at 75% Watt-max. This will be followed by 10 minutes of rest and then work to exhaustion will be performed at 90% watt max. Exhaustion will be defined as the point in time where the test person will no longer be capable of maintaining a pedal frequency of 80 revolutions per minute (RPM) at the workload of 90% watt max.

Intervention

During the bicycling exercise the test persons will be given 3.5 ml per kg body weight of a solution comprising 6% carbohydrate (maltodextrin) per 15 minutes. Additionally, the test persons will be given either 500 mg stevioside or 500 mg corn flower at the beginning of the bicycling exercise.

Blood Samples

Blood samples will be collected 0, 30, 60, 90, 120, 130 minutes from start of the bicycling exercise and at the time of exhaustion. After collection the samples will be centrifuged and the serum will be stored at −20° C. Parameters that will be evaluated in the blood samples will be content of glucose, insulin, glycogen, kreatine kinase, lactate dehydrogenase and myoglobin.

Example 2

Effect of Stevioside Intake on Muscle Glycogen Re-Synthesis During Physical Activity The aim of this experiment is to investigate if intake of stevioside in addition to a carbohydrate-containing composition after work related depletion of muscle glycogen will increase the rate of glycogen re-synthesis as compared with intake of the carbohydrate-containing composition alone.

Test Subjects 15 healthy and well trained male subjects will be selected for the study. The subjects will be completing the test procedure twice, on two separate days at least 7 days apart in a crossover design, where intervention—i.e. addition of stevioside to the restitution meal—is blinded and randomised for both the test subjects and the scientific staff.

Inclusion Criteria:

Well trained, healthy exhaustive trained males, age 18 to 40.

Exclusion Criteria:

Persons suffering of a metabolic disease, which is related to the carbohydrate metabolism, such as diabetes type 1 or 2, insulin resistance and the like, cannot be included in the test. Also persons, who are prescribed a medical drug or diet supplement that could affect the carbohydrate metabolism, will be excluded from the study. Finally persons that are not capable of completing the fasting period or the test design will be excluded from the study.

Before Testing

Before testing the VO2-max and maximal pulse will be determined for each test subject. The results of this test will be used for determination of the working load for each test subject during the test.

The test will be performed for at least 72 hours before the bicycling test is commenced.

Experimental Design:

The bicycling test is designed as a working session having the purpose of completely depleting the muscle glycogen storage of the working muscles. The depletion of muscle glycogen will be further facilitated by a twelve hours fasting period prior to commencement of the bicycling test.

The test persons will be completing the test twice on two separate days at least 7 days apart in a crossover design, where the intervention—i.e. the additional intake of stevioside together with the carbohydrate-containing composition during the bicycling work—is blinded and randomised for both the test subjects and the scientific staff.

During the working session the test subjects will be exercising for 2 hours on a bicycle ergometer at 65-75% of VO2-max. Afterwards these two hours of bicycling exercise, the persons will be performing a number of one minute intervals at maximum workload. Every interval will be followed by a one minute break, where the subjects pedal at low intensity of own choice. This interval exercise will be continued until the test subject's plasma glucose is below 3.89 mmol/l. This value is selected to ensure that the glycogen storage in the liver is depleted to identical extent in each test.

Immediately after the working session the test subject will be given a carbohydrate-containing composition that comprises 2 g carbohydrate per kg of body weight. Also 2 hours after completion of the working session the test persons will be given a carbohydrate-containing composition that comprises 2 g carbohydrate per kg of body weight. These compositions will be added either 500 mg stevioside or placebo (starch corn).

Tissue and Blood Samples

Before the working session will be commenced blood samples will be collected together with muscle biopsies in order to determine the content of plasma glucose, plasma insulin, and muscle glycogen before commencement of the bicycling workload. Further blood samples will be collected at 0, 30, 60, 90, 120, 150, 180, 210 and 240 minutes after completion of the working session, and further muscle biopsies will be collected at 0, 120 and 240 minutes after completion of the working session.

After collection the blood samples will be centrifuged and the serum will be stored at −20° C. Parameters that will be evaluated in the blood samples will be content of glucose, insulin, glycogen, kreatine kinase, lactate dehydrogenase and myoglobin.

After collection of the muscle biopsies the samples will be stored under liquid nitrogen. The parameter evaluated in the muscles biopsies will be glycogen.

Example 3

Effect of Stevioside Intake on Increase of the Muscle Mass

The aim of this experiment is to investigate if intake of stevioside in addition to a protein-containing composition will have a positive effect by increasing the muscle mass.

Test Subjects

Elderly human being of an age ranging from 65 to 95, both males and females, will be selected for the study.

Inclusion Criteria:

Elderly and healthy people, age 65 to 95. Also test subjects suffering of hypertension, hyperlipidaemia or type 2 diabetes may be included in the test.

Exclusion Criteria:

Elderly people suffering of a disease relating to low cognitive function, orthopaedic surgical disease and pharmacological treatment where exogenous testosterone or any other active substance known to affect muscle mass is administered. Moreover, the test subjects must not suffer of any musculoskeletal disorder and the like.

Test Design:

The test will be performed during 12 weeks, where the test subjects will subjected to exercise 3 days a week, where each exercise is separated by at least one day. The test will be performed in groups of 20-30 subjects. During the first week the test subjects will be taught how to perform the exercises correctly on the machines at low weight, where the test subject. Thereafter the weight is increased to such an extent that the test person is able to repeat exercise 6-8 times. In the following weeks the weight is increased (approximately 5-10% per week) so that the number of repetitions are kept at 6-8. The test subjects will be subjected to ten different exercises, all of which will be performed in machines with weights for strengthening the muscles.

The test subjects will be given a liquid composition immediately after completion of the exercises. Two different liquid compositions will be tested. One liquid composition of approximate 250 ml will comprise whey protein, maltodextrin and steviol glycosides (500 mg) and the other liquid composition of approximate 250 ml will comprise whey protein and maltodextrin together with a sweetener. The test will be blinded and randomised.

Body Composition:

The body composition of each test person will be determined by use of dual energy x-ray absorption (DXA, Hologic QDR-2000 plus, Hologic Inc., Waltham, Mass., USA) and MR scanning of the muscles in the legs and arms.

Muscle Strength:

The muscle strength and knee extensor muscle strength will be evaluated. Quadriceps strength will be tested using an isokinetic dynamometer (kin-Com 500H Chattanooga).

Biochemical Analysis:

The test persons will be instructed to avoid exhausting exercise and intake of alcohol the day before collection of fasting blood samples. The blood samples will be centrifuged and stored at −80° C. until the samples are analyzed. Parameters that will be evaluated in the blood samples will be content of glucose, insulin, triglycerides, total cholesterol, high-density lipoprotein, insulin growth factor I (IGF-1).

Example 4

Effects of Stevioside on Glycogen Restitution after Long-Term Exercise

In this example, the effect is examined of a 500 mg steviol glycosides supplementation together with post-exercise oral carbohydrate (1.5 g/kg/h), versus an isocaloric carbohydrate supplementation on muscle glycogen resynthesis, following glycogen depletive exercise. Fifteen trained male cyclists performed two cycling sessions of 120 min at 75-85% Vo2-max, with the post exercise supplementation of stevioside organized in a double blinded crossover study design. Over the course of a 4 h of recovery period, muscle biopsies were obtained from the vastus lateralis immediately and 240 minutes after exercise, to measure post-recovery glycogen concentration and rate of post-exercise glycogen synthesis. In order to measure plasma glucose, insulin and glucagon, blood samples were drawn before and immediately after exercise, and at every half hour during the four hour recovery period. Results A significant increase in total glycogen concentration was seen following the 4 hour of recovery in both trials ($p<0.005$). Glycogen resynthesis following 4 h of recovery showed a clear tendency in the rate of glycogen repletion (27.96±2.60 mmol/kg/h and 37.84±3.72 mmol/kg/h for placebo and stevioside supplementation $p<0.002$). Plasma glucose and glucagon levels also show a reduction when stevioside was supplied. Conclusion: The addition of stevioside to oral CHO feedings increase significantly post-exercise muscle glycogen resynthesis or rate of glycogen repletion, $p<0.022$.

INTRODUCTION

Based on the above information the aim of the present study was to investigate the hypothesis that the acute supplementation of the steviol glucoside—stevioside, to post exercise carbohydrate feeding, will further increase the glycogen resynthesis rate compared to intake of carbohydrate alone.

Methods

Subjects:

In this example, nine healthy and well trained male participants was included, age 25±3 years, weighing 77.5±7.7 kg, were recruited for the study through advertising on the webpages of local cycling, triathlon and mountain bike clubs in the area of Aarhus, Denmark. Comprehensive verbal and written explanation, of the aim and content of the study as well as the potential risks and discomforts associated with participating in the study were given, before all subjects gave their written informed consent to be enrolled in the study. The experimental protocol was approved by "The Central Denmark Region Committees on Health Research Ethics".

The following criteria were set for inclusion in the study: Subjects should be male, between 18 and 40 years of age, be accustomed to cycle training at low and high intensity workloads, have a VO2-max of 50 ml·kg-1·min-1 or higher at the initiation of the study (measured by an initial incremental VO2-max test on an ergometer bike). Furthermore the subjects should be free of any metabolic diseases relating to carbohydrate metabolism, and not be taking medication and/or food supplements in any form that could affect carbohydrate metabolism. The subjects' performance characteristics are presented in table 1a. Female subjects were not included in the study, as we wanted to rule out any gender dependent physiological differences that could bias the results of the study. All of the nine subjects completed the entire protocol, and all data from all subjects have been included in the analysis. Subject's performance characteristics are presented in table 1.

TABLE 1

Anthropometric and performance characteristic of study participants n = 9
All of the nine subjects completed the entire protocol.

| Anthropometric characteristics | Mean ± SD |
|---|---|
| Age [years] | 25 ± 3 |
| Weight [kg] | 77.5 ± 7.7 |

TABLE 1-continued

Anthropometric and performance characteristic of study participants n = 9
All of the nine subjects completed the entire protocol.

| Anthropometric characteristics | Mean ± SD |
|---|---|
| $VO_2$-max [ml/min$^{-1}$] | 4765 ± 331 |
| $VO_2$-max [ml · kg$^{-1}$ · min$^{-1}$] | 62 ± 7 |
| Watt-max | 379 ± 24 |

Experimental Design

In the present study, a double blinded crossover protocol was used to examine the effect of post exercise carbohydrate ingestion supplemented with or without stevioside supplementation on muscle glycogen resynthesis. The double blinded crossover protocol was chosen to ensure a satisfactory statistical power with the relative few subjects that were included in this study. After completing a preliminary anthropometric assessment incremental and VO2-max test, each subject completed two randomized experimental trials; separate by at least seven days.

Preliminary Testing

An incremental exercise test (20 W·min-1) was performed on a computer-controlled electromagnetically-braked cycle ergometer (Excalibur Sport, Lode, Groningen, NL) to voluntary exhaustion. Prior to conducting the incremental test procedure the subjects performed a thorough warm-up. The warm-up consisted of a 10 minutes bike ride on the ergometer bike used for the VO2-max test starting with a fixed workload of 100 Watt. Immediately after completion of the warm-up the subject starts the incremental VO2-max test, with an initial work load of 100 watt where after the work load are increased by 20 watts a minute until voluntary exhaustion, at which point the test was terminated. VO2-max and watt max was determined as the highest 15 seconds average during the test. Strong verbal encouragement was given throughout the test Throughout the incremental test inspired and expired volumes (bi-directional turbine, Jaeger TripleV, Hoechberg, Germany) and gas concentrations (chemical fuel cell (O2) and infrared (CO2) analyzers; Jaeger Oxycon Pro, Hoechberg, Germany) were sampled at 50 Hz, with the time-aligned volume and gas concentration signals allowing online calculation of breath-by-breath pulmonary gas exchange and ventilatory variables (e.g. O2 uptake (VO2), CO2 output (VCO2) and ventilation (VE)). Prior to each test the gas analyzers were calibrated with one precision-analyzed gas mixture and room air to span the concentration range observed during exercise, with the turbine volume sensor calibrated using a 3-liter syringe (Hans Rudolph, Kansas City, Mo.).

This test used for determination of maximal oxygen uptake (VO2-max), from the average VO2 for an integral number of breaths over the final ~15 s of the incremental phase. The preliminary test protocol was carried out at least 72 hours before initiation of the experimental protocol, and served to 1) ensure that the subjects adhered to the inclusion criteria, 2) determine individual values for VO2-max, watt-max and maximal heart rate which were used to calculate the work load to be used during the experimental protocol. All preliminary testing was carried out by Søren Lavrsen Experimental and Supplementation Protocol After the preliminary testing, each subject underwent two experimental trials, with the experimental supplementation randomized using a randomizing software (Research randomizer) and blinded to both subject and researchers by supplementing the stevioside concealed in capsules. The capsules were color coded according to their content, codes of the supplementation were not revealed to the researchers or laboratory personnel until all data analysis was completed. The two experimental trials were separated by at least seven days. The subjects were instructed to refrain from any intense exercise 24 hour before both the preliminary test and the two experimental trials. The subjects were also instructed to follow their normal diet during the last 48 hours leading up to both the preliminary test as well as the 12 hour fast preceding the experimental trials.

As illustrated the table below, the subjects arrived fasting at 8:00 o'clock a.m. in the lab and completed a glycogen depletion ride consisting of 120 minutes cycling at 75%-80% of their maximal heart rate reserve, followed by a series of five 30 seconds sprint interval at an all-out intensity interspaced with a rest period of 60 seconds. Workload and target heart rate zone was calculated for the subjects, based on the results presented in table 1, performance characteristics of the subjects. The depletion ride was done on a mechanically breaked SRM ergometer bike (Schoberer Rad Mestechnik—SRMGmbH Jülich, Germany). The subjects were allowed only water during the depletion ride.

Illustration of the Experimental Protocol

| 12 hour fast Depletion protocol | Time [minutes] | | | | | | | | |
|---|---|---|---|---|---|---|---|---|---|
| | 0 | 30 | 60 | 90 | 120 | 150 | 180 | 210 | 240 |
| Cabohydrate supplementation | ↑ | | ↑ | | ↑ | | ↑ | | |
| Muscle biopsy | ↑ | | | | | | | | ↑ |
| Plasma glucose | ↑ | ↑ | ↑ | ↑ | ↑ | ↑ | ↑ | ↑ | ↑ |
| Plasma insulin | ↑ | ↑ | ↑ | ↑ | ↑ | ↑ | ↑ | ↑ | ↑ |
| Plasma glucagon | ↑ | ↑ | ↑ | ↑ | ↑ | ↑ | ↑ | ↑ | ↑ |

Before the subjects started the depletion ride, blood was drawn from a medial antecubital vein to establish baseline values for plasma glucose, plasma insulin and plasma glucagon concentrations. After completion of the depletion ride and 240 minutes later, a muscle biopsy was obtained from the vastus lateralis muscle by the use of a percutaneous needle biopsy technique, using the protocol described by Bergström (Bergström 1962). The biopsy sampling was performed by a trained physician with extensive experience in sterile technique. An area of anterolateral side of one thigh was disinfected with chlorhexidine, and local anesthetized with lidocaine (10 mg/ml) in the skin, subcutaneous tissue and muscle fascia. After the area was covered with a sterile hole-piece, a small incision in the skin and fascia of the leg was made with a scalpel and a tissue sample was taken with a Bergström biopsy needle with the aid of suction. The biopsy procedure was managed by Mikkel Overgaard, and assisted by Søren Lavrsen. Approx. 100 mg of muscle tissue was taken from the vastus lateralis muscle. The muscle tissue samples were weighted and immediately placed in liquid nitrogen, and then transferred to a freezer (–80° C.) for storage until analysis for determination of glycogen concentration would be made. At the same time a polyethylene catheter was placed subcutaneous into a medial antecubital vein from which blood samples were collected. 10 ml of blood were drawn for the analysis of plasma glucose and insulin, and 7.5 ml of blood was drawn for the analysis of plasma glucagon. After the first sample at 0 minutes, blood was drawn at 30, 60, 90, 120, 150, 180, 210 and 240 minutes after the subject has finished the glycogen depletion protocol. Blood samples were centrifuged before 2 ml of the plasma was pipetted into standard analyzing tubes and stored at −80° C. for later analysis.

Immediately after the muscle biopsy procedure and initial blood sampling, the subjects ingested either 500 mg of steviol glucosides, or placebo (500 mg of corn starch) Supplementation, together with 1.5 gr/body weight of liquid maltodextrine solution (Pure Power, Harre Denmark). The sequence of stevioside and placebo supplementation was randomized in a balanced order. At 60, 120 and 180 minutes after termination of the depletion ride, the subjects received another carbohydrate rich feeding (1.5 gr/body weight/hour of Carbohydrates/kg body weight/hour), in accordance with the guidelines recommended by (Ivy et al. 1988).

Supplementation:
Carbohydrate Source

The carbohydrates were derived from a mixture of liquid maltodextrines (PurePower, Harre, Denmark) and a standardized meal of solid high glycemic foods (90 gr of white bread and 15 gr sugar sweetened fruit spread). The carbohydrate drink was prepared in accordance with the manufactures guidelines in order to ensure an identical fluid volume at both trials, as change in volume could alter gastrointestinal absorption rate. Supplying part of the carbohydrates as solid food was chosen as we found through a pilot study, that supplying the subjects with only liquid carbohydrates, after 12 hours of fasting and completion of the depletion protocol, could cause gastrointestinal distress, nausea and vomiting in the subject, which could interfere with the results of the study, through other means than the processes which we wanted to examine.

Stevioside

For this study steviol glycosides containing: 91% of stevioside, 4% rebaudioside A and 5% of other steviol glucosides (99.8% pure from Steviafarm Industrial S/A, Maringa, Parana, Brazil) was supplemented to the subjects, together with liquid maltodextrine immediately after the first muscle biopsy. As steviol glycosides used in this study has a taste 300-350 times sweeter than sucrose, it was chosen to supplement it concealed in capsules, in order to blind the interventions for both researchers and study subjects.

Muscle Tissue Preparation, Glycogen Analysis and Calculations

The Glycogen content was be determined by an acid-hydrolysis method as described by Passonneau and Lowry (Passonneau & Lowry 1972. As illustrated below, glucose, the hydrolysis product of glycogen, is converted into glucose-6-phosphate (G-6-P) by hexokinase in the presence of ATP. In the presence of nicotinamide adenine dinucleotide (NAD), G-6-P is oxidized by the enzyme glucose-6-phosphate dehydrogenase (G-6-PD) to 6-phosphogluconate and reduced nicotinamide adenine dinucleotide (NADH). The increase in NADH concentration is directly proportional to the glucose concentration and can be measured spectrophotometrically at 340 nm using a Beckmann spectrophotometer (at 340 nm) to express the glycogen content of the analyzed muscle sample.

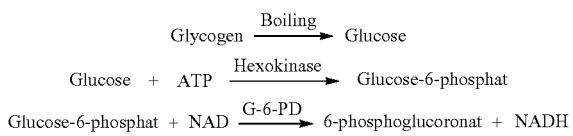

Preparatory Procedure:

In preparation for glycogen analysis, a portion of each muscle sample was freeze-dried in a desiccator for 48 hours. Once removed from the desiccator non-muscle elements such as blood and connective tissue was removed. Muscle material was weighed and placed in heat resistant tubes and covered with 0.5 ml 1M HCL. Tubes containing the freeze-dried muscle sample and HCL were then heated in a water bath for 150 minutes at 100° C. to hydrolyze the glycogen into glucose unites. Thereafter, the samples were cooled in an ice bath for 20 minutes, before they were whirl-mixed and then centrifuged at 3500 g for 10 minutes at 4° C. Hereafter, 20 µl of the supernatant was transferred to the analysis cuvettes by use of an air displacement pipette. 500 µl of a reagent was then added to all cuvettes.

Analysis

The initial light absorbency rate of the solution (A1) was recorded using a Beckmann spectrophotometer at 340 nm (a H2O filled cuvette is used as reference). Hereafter 5 µl of diluted Hexokinase was the added to the solution and the cuvettes. After 60 minutes the light absorbency rate of the solution is the recorded again (A2) using the spectrophotometer at 340 nm. Søren Lavrsen assisted with in analysis procedure.

Calculations

The light absorbency rates, recorded by use of spectrophotometer and weight of the muscle sample were used to calculate the glycogen concentration using following equation (all calculation was made by Søren Lavrsen):

$$c = \frac{V \times F}{e \times d \times v} \times \Delta A = \frac{\text{mmol}}{\text{kg}} \text{ muscle}$$

$$c = \frac{0.525 \times 0.5 \times 1000}{6.3 \times 1 \times 0.020 \times \text{muscle weight}} \times \Delta A = \frac{\text{mmol}}{\text{kg}} \text{ muscle}$$

$$c = \Delta A \times \frac{2083}{\text{muscle weight}} = \frac{\text{mmol}}{\text{Kg}} \text{ muscle}$$

Where:
$\Delta A = A_1 - A_2$
V=total volume[ml]
V=sample volume[ml]
D=light distance [cm]
e=extinction coefficient for NADH at 3.40 nm=6.3 [1× mmol⁻xcm⁻¹]
F=dilution factor (0.500 ml 1M HCL/~2 mg muscle tissue)

Reagent:

| | |
|---|---|
| 1. Tris-buffer 1M | 15.0 ml |
| 2. Distilled H₂O | 67.5 ml |
| 3. ATP 100 mM | 450 µl |
| 4. MgCl₂ | 900 µl |
| 5. NAD 100 mM | 90 µl |
| 6. G-6-PD | 60 µl |

Enzyme:

| | |
|---|---|
| 1. Hexokinase | 30 µl |
| 2. Distilled H₂O | 900 µl |

Plasma Analysis

Blood samples were collected for the measurements for measurement of the plasma glucose, insulin and glucagon values before initiation of the glycogen depletion protocol and at 0, 30, 60, 90, 120, 150, 180, 210 and 240 minutes after the subject has finished the glycogen depletion protocol.

10 ml of blood were drawn for the analysis of plasma glucose and insulin, and 7.5 ml of blood was drawn for the analysis of plasma glucagon. All blood was drawn from the antecubital vein. For glucose and insulin the drawn blood was collected in lilthium heparinized tubes (Venosafe—plasma VF-109SHL, Terumo Europe N.V., Leuven, Belgium). For glucagon the drawn blood was collected in EDTA treated tubes (Venosafe). With all samples the tubes were turned over 10 times, to avoid coagulation, before they were centrifuged at 1500 G for 10 minutes at 5° C. using a Sigma 3-18 centrifuge (Sigma Laborzentrifugen GmbH, Osterode am Harz, Germany). 2 ml of the plasma was pipetted into standard analyzing tubes and stored at −80° C. for later analysis. After all testing sessions were finished; all blood samples were packed, according to regulations, in an icebox at 20° C., and transported to the Diabetes laboratory 4, at Aarhus University Hospital, Tage-Hansens Gade (Aarhus, Denmark) for analysis of plasma glucose, insulin and glucagon concentration.

Insulin Assay

Insulin was analyzed by radioimmunoassay using guinea pig anti-porcine insulin antibody (Novo Nordisk, Bagsvrd, Denmark) and mono-125I-(Tyr A14)-labeled human insulin (Novo Nordisk) as tracer and rat insulin as standard (Novo Nordisk). Bound and free radioactivity was separated by ethanol. The inter- and antra-assay variation coefficients were both less than 5%. Stevioside did not interfere with insulin assay at the studied concentrations.

Glucagon Assay

Glucagon was analyzed by radioimmunoassay kit (Millipore Research, Park Drive, St Charles, Mo. USA) according to manufacturer's instructions. The glucagon antibody is specific for pancreatic glucagon and has no cross-reaction with other islet polypeptides. The limit of sensitivity for glucagon assay is 20 pg/ml.

Statistical Analysis

Glucose, insulin and muscle glycogen were analyzed using 2-tailed dependent T-test. The difference in the overall rate of muscle glycogen resynthesis was analyzed with a 2-tailed dependent T-test. Statistical significance was established using an alpha level of $p<0.05$. Data were analyzed using Grafpad, Prism4 for Windows. All data are presented as means±SE.

Results

Power Output and Heart Rate Response

There were no differences in average relative power output between the two protocols: 69%±1% for the placebo protocol and 72%±2% for the stevioside protocol. These workloads caused an average heart rate response of 73%±2% in the placebo protocol and 74%±2% of hr-max in the stevioside protocol. There were no significant differences between the placebo and stevioside protocol.

Muscle Glycogen Concentration and Glycogen Resynthesizes Rate

A clear difference was observed in muscle glycogen concentration among the two intervention groups at 240 minutes after initiation of the recovery protocol. 240 minutes after completion of the depletion protocol the muscle glycogen concentration for the placebo intervention reached 246.4±20 mmol/kg/dw and 281.5±29 mmol/kg/dw for the stevioside intervention, cf. FIG. 1 top panel.

Difference in glycogen resynthesis rate during the recovery period, measured as mmol/kg/h, was interestingly significantly higher for the stevioside supplementation compared to placebo supplementation, FIG. 1 bottom panel ($p<0.022$). For the placebo the glycogen synthesis rate was 27.96±2.6 mmol/kg/h and for the stevioside supplementation the rate was 37.84±3.72 mmol/kg/h. The glycogen resynthesis rate was increased 35%, which is very unique (see FIG. 1).

Plasma Glucose (Nine Participates, not all Samples Analyzed)

Figure 2:
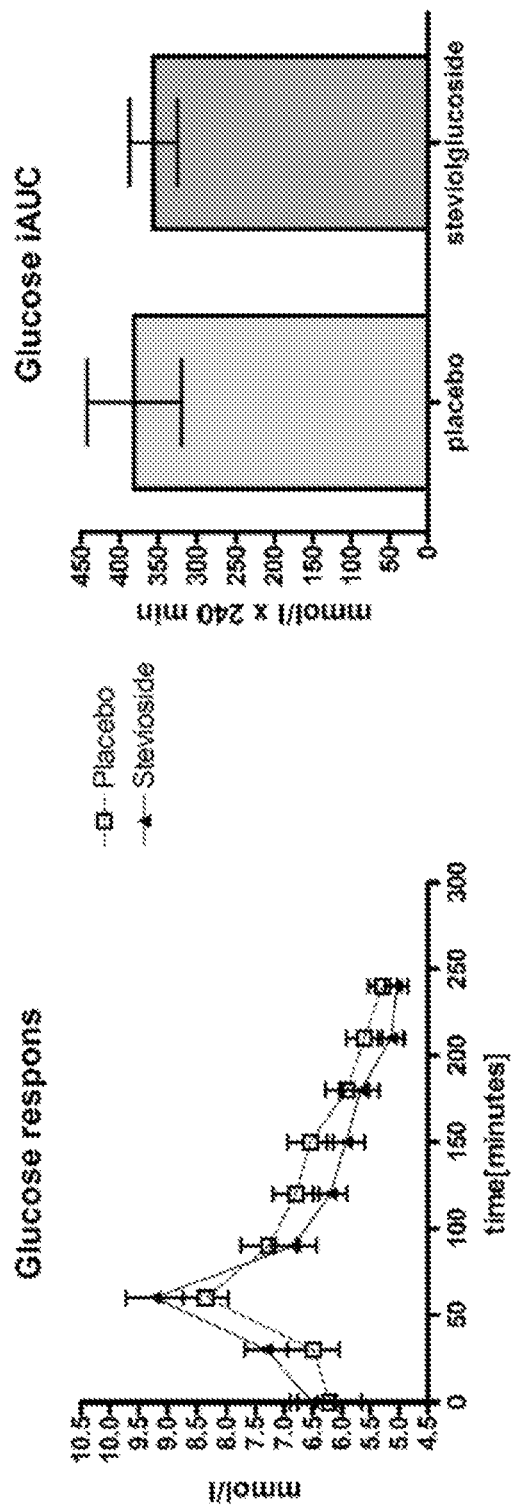
FIG. 2. Plasma glucose response during the four hour recovery period, expressed as incremental area under the curve (iAUC). The figure illustrates the pattern in plasma glucose response for both of the interventions—placebo and stevioside during the four hour recovery period of the trial.

Plasma glucose response during the four hour recovery period, expressed as incremental area under the curve (iAUC), tend to be affected by stevioside ingestion, as the glucose level was lower for the stevioside group. Due to the low power (not all participants was included in this study), the difference did not show statistical significance. It is expected that the difference will be significant when all participants are included. FIG. 2 illustrates the pattern in plasma glucose response for both of the interventions—placebo and stevioside during the four hour recovery period of the trial.

Plasma Insulin (Nine Participates, not all Samples Analyzed)

Figure 3:
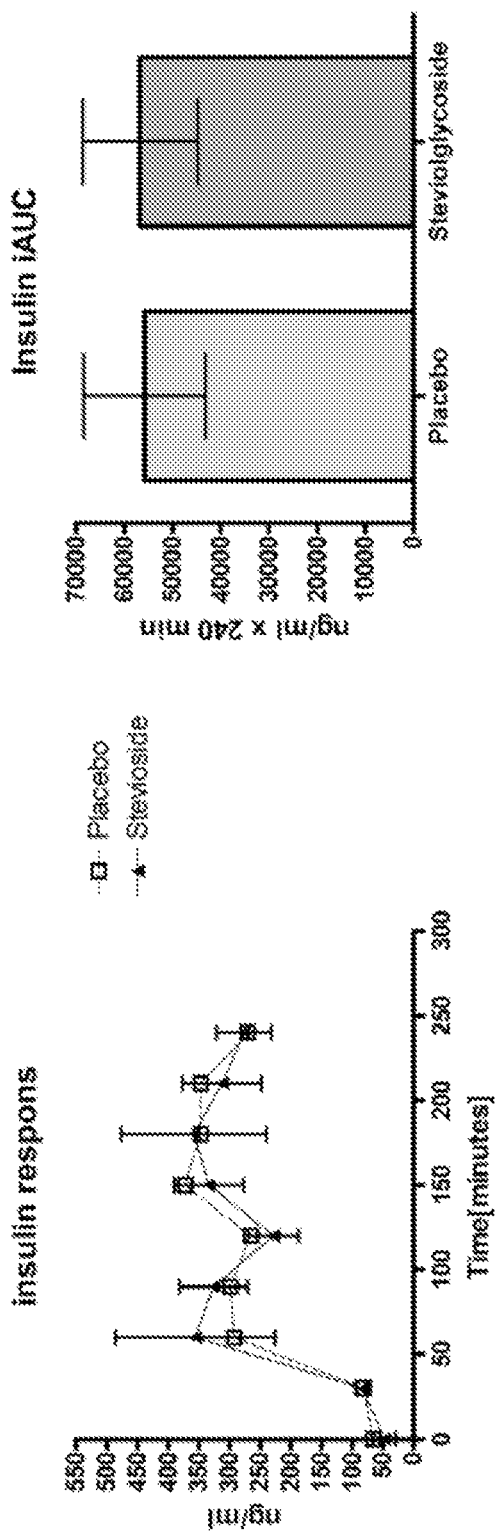
FIG. 3. Plasma insulin response during the four hour recovery period, expressed as incremental area under the curve (iAUC). Difference in plasma insulin concentration between stevioside and control at any times during the recovery period, expressed as incremental area under the curve (p=0.95).

There was no significant difference in plasma insulin concentration between stevioside and control at any times during the recovery period, expressed as incremental area under the curve ($p=0.95$). Mean area under the curve was 55790±12660 ng/ml*4 hours and 56720±11950 ng/ml*4 hours for placebo and stevioside respectively. As shown in FIG. 3; 30 minutes after ingesting the first carbohydrate supplement, the plasma insulin concentration increased significantly, reaching the highest concentration at 60 minutes after the first CHO supplementation. Another increase in insulin plasma concentration follows the third CHO feeding at 120 minutes with the peak concentration reached at 150 minutes for the placebo protocol and at 180 for the stevioside protocol respectively. From here the insulin plasma concentration decline steadily for both the placebo and the stevioside supplementation protocol.

Plasma Glucagon (Nine Participates, not all Samples Analyzed)

Figure 4:
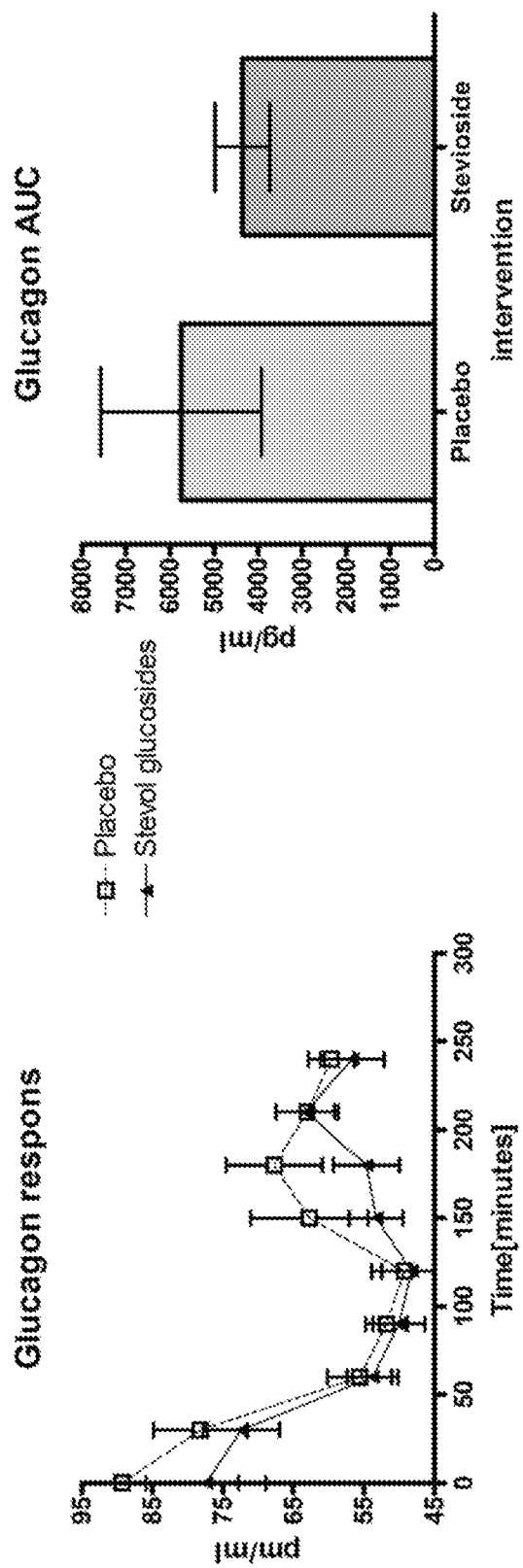
FIG. 4. Plasma glucagon response during the four hour recovery period, expressed as incremental area under the curve (iAUC).

The mean plasma glucagon concentration expressed as area under the curve was clearly reduced in the *stevia* group; cf. FIG. 4 left panel. Not all participants was included in this example, which reduce the statistical power, however, it is expected that the difference will be significant when all participants are included.

DISCUSSION

The primary finding of the present example is that supplementation of stevioside, in addition to carbohydrate, after exhaustive glycogen depleting exercise, increase muscle glycogen resynthesis significantly ($p<0.022$) over a four hour recovery period (all fifteen participants). In addition, stevioside supplementation over this period appears to alter blood levels of glucose and glucagon but not insulin levels.

The invention claimed is:

1. A method for treatment of muscle glycogen depletion and/or loss of muscle mass in a human subject in need thereof, the method comprising the step of orally administering to the human subject a composition comprising an effective amount of a steviol glycoside and/or an aglycone thereof and a high glycemic carbohydrate, wherein said steviol glycoside and/or aglycone thereof is selected from the group consisting of rebaudioside A, rebaudioside B, rebaudioside C, rebaudioside D, rebaudioside E, rebaudioside F, dulcoside A, steviol, isosteviol, stevioside, steviolbioside, rubusoside, and mixtures thereof.

2. The method according to claim 1, wherein the steviol glycoside is stevioside.

3. The method according to claim 1, wherein the carbohydrate is maltodextrin.

4. The method according to claim 1, wherein the composition further comprises protein.

5. The method according to claim 4, wherein the protein is whey protein.

6. The method according to claim 1, wherein the composition further comprises electrolytes.

7. The method according to claim 1, wherein the composition is administered as a solid, frozen, semi-solid, or liquid composition.

8. The method according to claim 7, wherein the composition is a liquid composition selected from the group consisting of milk obtained from animals, milk products derived from soy, rice, coconut or other plant material, fermented milk products and drinking chocolates.

9. The method according to claim 7, wherein the composition is a liquid composition selected from the group consisting of sports drinks, beverages, refreshing beverages, carbonated water, flavoured water, carbonated flavoured water, drinks containing fruit or vegetable juice or nectar, vitamin enhanced sports drinks, high electrolyte sports drinks, highly caffeinated high energy drinks, coffee, decaffeinated coffee, tea, tea from fruit products, tea derived from herb products and decaffeinated tea.

10. The method according to claim 7, wherein the composition is a solid composition selected from the group consisting of chocolate and nutritional bars, drops, candies, cookies, cereals, snack bars and biscuits, or a frozen composition selected from the group consisting of frozen desserts, ice creams, ice sherbets and ice shavings, or a semi-solid composition selected from the group consisting of cream, jam and gels, yoghurt, pudding and jelly.

11. The method according to claim 1, wherein the composition is administered prior to, and/or during and/or following exercise.

12. The method according to claim 1, wherein the human subject is selected from the group consisting of endurance athletes, team sports athletes, athletes participating in weight class regulated sports, professional cyclists, professional football players, and ice hockey players.

13. The method according to claim 1, wherein the human subject is an elderly person.

14. The method according to claim 1, wherein the rate of glycogen re-synthesis is increased in muscles that are depleted in glycogen due to exhaustive exercise.

15. The method according to claim 14, wherein lost muscle mass is restored.

* * * * *